United States Patent [19]

John

[11] Patent Number: 4,705,049
[45] Date of Patent: Nov. 10, 1987

[54] INTRAOPERATIVE MONITORING OR EP EVALUATION SYSTEM UTILIZING AN AUTOMATIC ADAPTIVE SELF-OPTIMIZING DIGITAL COMB FILTER

[76] Inventor: Erwin R. John, 930 Greacen La., Mamaroneck, N.Y. 10543

[21] Appl. No.: 892,993

[22] Filed: Aug. 4, 1986

[51] Int. Cl.$^4$ .................................................. A61B 5/04
[52] U.S. Cl. ...................................... 128/731; 364/417
[58] Field of Search ................. 128/731, 732; 364/417

[56] References Cited

U.S. PATENT DOCUMENTS 4,603,703  8/1986  McGill et al. ........................ 128/731

OTHER PUBLICATIONS

John et al., "Normative Values ... Detection", *Electroen & Clin. Neur.*, 1982, 54: 153–160.
Friedman et al, "Application of Digital ... Potential", *Electroen & Clin Neur.*, 1982, 53: 405–416.
Wallingford et al, "A Dynamic ... Analyzer", *IEEE Trans Instr. and Measurement*, vol. 27, No. 1, Mar. 1978, pp. 70–73.
Wheeler et al, "Real-Time ... Neural Signals", *Med. & Biol Eng & Comp.*, May 1985, pp. 243–247.
Hamer et al, "Digital Filtering of Phys. Signals ... ", *Med & Biol Eng & Computing*, pp. 274–278, May 1985.

*Primary Examiner*—Lee S. Cohen
*Attorney, Agent, or Firm*—Eliot S. Gerber

[57] ABSTRACT

An electroencephalograph (EEG) system for the detection of a patient's brain waves includes a group of electrodes removably attached to the patient's scalp, low-noise high-gain amplifiers and analog/digital converters. A digital comb filter is used to improve the signal-to-noise ratio and has self-optimizing capability. In the digital comb filter, the band pass frequencies are automatically selected by comparing, at each tooth of the comb, the phase variance parameter, under the brain conditions of the presence and absence of a synchronized stimulus producing an evoked potential brain wave.

7 Claims, 7 Drawing Figures

INTRAOPERATIVE MONITORING OR EP EVALUATION SYSTEM UTILIZING AN AUTOMATIC ADAPTIVE SELF-OPTIMIZING DIGITAL COMB FILTER

BACKGROUND OF THE INVENTION

The present invention relates to medical devices and more particularly to an improvement in EEG (electroencephalograph) devices used for evoked potential (EP) analysis. EP's are transient oscillations of the EEG which are time locked to the presentation of sensory stimulation. The waveshape of this oscillation, imbedded in the EEG, reflects the processing of that stimulus information by the brain. Successive components of the EP waveshapes represent the passage of incoming neuronal activity along particular anatomical pathways. For this reason, precise knowledge about EP waveshapes can provide a sensitive index of the functional status of neuroanatomical structures. In order to utilize such information most advantageously, for example, to monitor the condition of certain brain regions during neurosurgery, the EP waveshape must be separated and extracted from the other electrical activity in which it is embedded as quickly and as cleanly as possible. Because EP waveshapes are complex and vary depending upon stimulus parameters, neural condition and characteristic of individual patients, it is also advantageous to obtain objective criteria for evaluation of changes in EP waveshape during a critical period of observation, such as during an operation on the brain. At times, it is desirable to obtain such EP's from as many as 19 electrodes simultaneously, to compare the response in different kinds of stimuli sequentially in order to evaluate different neuroanatomical pathways. A major problem in such analyses is the poor signal-to-noise ratio.

One method that is used to improve the signal/noise ratio of evoked potentials is signal averaging. In evoked potential (EP)analysis, a large number of stimuli, such as light flashes or auditory clicks, are presented to the patient in a regular pattern, for example, 2048 auditory clicks at repetition rates about 7-10/second. The brain response, for example, the brain stem auditory evoked potential (BAEP), is in synch with the stimuli, but the noise is random. When the responses are averaged, the noise tends to cancel itself out, leaving an improved signal/noise ratio. This improvement is proportional to the square root of the sample size. Because the time required to achieve useful improvement of S/N is so long relative to the time frame of intraoperative events, conventional signal averaging is poorly suited for surgical monitoring. Further, significant fluctuations in the functional status of brain regions may occur during the long period required to accumulate a sufficiently large sample and the corresponding heterogeneous waveshapes are obscured by combination within the average EP finally obtained.

Even with signal averaging, the signal/noise ratio may not be sufficient for reproducible results, under some circumstances, as suggested in an article by Drs. E.R. John, H. Baird, J. Friedman and M. Bergelson entitled "Normative Values For Brain Stem Auditory Evoked Potentials Obtained By Digital Filtering And Automatic Peak Detection", *Electroencephalography and Clinical Neurophysiology* 1982, 54:153-160 (1982, Elsevier Sci. Pub. 0013-4949). Further improvement of the signal/noise ratio by increasing the sample size is prohibitively time-consuming.

An article entitled "Application of Digital Filtering and Automatic Peak Detection to Brain Stem Auditory Evoked Potential", Friedman, John, Bergelson, Kaiser, Baird; *Electroencephalography and Clinical Neurophysiology*, 1982, describes a way to achieve rapid improvement of S/N by using a digital bandpass filter with optimal bandwidth to suppress some noise components. This article describes an analysis of averaged brain stem auditory evoked responses. The same method can be applied to any type of EP. Repeated samples of signal (presence of stimulus) and noise (absence of stimulus) were subjected to FFT (Fast Fourier Transform). At each frequency, the variance of phase was computed separately for the sets of signal samples and noise samples. The optimal frequency band, for digital filtering, was obtained by comparing phase variance (as a function of frequency) in the absence of stimulus against phase variance in the presence of stimulus. Phase variance is low at frequencies which contribute to the waveshape of the evoked potential (which is phase-locked to the stimulus), while the phase variance of noise components is high because of its random composition. The optimal digital filter is defined as the frequency band within which the phase variance is lowest for samples of signal and highest for samples of noise. Once the filter ("filter window") has been selected, subsequent samples of signal are decomposed by FFT (Fast Fourier Transform) and an Inverse Fast Fourier Transform (IFFT) is then performed using only the terms inside the selected filter window. The signal which has been decomposed into its spectral components by FFT is thus reconstructed with the noise selectively removed. In contrast to conventional signal averaging methods, in which noise is reduced by summation of random variations, optimal digital filtering is selective removal of noise. It should be noted, however, that some noise components generated by the stimulator of the EP apparatus or reflecting high harmonics of other apparatus may have relatively low variance within the selected frequency domain.

In order to use this technique, the frequency "window" (band pass of frequencies) of the optimum filter was selected, using visual inspection by the operator, based on his visual reading of the phase variance diagrams and his experience. Those frequencies below and above the selected band were canceled (band rejection). The operator, if experience and careful, was able to select a frequency band that would improve the signal/noise ratio by selecting a band pass in which the signal was relatively strong compared to the noise.

That system has two major shortcomings. The first is that it requires the operator to visually inspect the phase diagram to select the optimal filter bandwidth (frequency window) so that the system relies upon the judmgent, skill and attention of a human operator. However, the time of such skilled operators is expensive, such a person may not be available during every surgical operation, and the person's judgement and attention may be less than perfect at times, especially during a prolonged operation.

The second problem is that, even if the band pass is correctly selected, it does not eliminate noise which is in phase synchronism with the signal. Such phase synchronous noise may lie within the optimal band pass. For example, components of stationary noise, such as from the harmonics of 60 Hz from operating room instruments or the evoked potential apparatus itself, may be in relatively stable phase and at the same frequency as components of the brain wave signal that it is desired to detect. Such synchronous noise is reincorporated into the signal, instead of being reduced by the filtering and averaging process.

OBJECTIVES AND FEATURES OF THE INVENTION

It is an objective of the present invention to provide an EP system in which faint evoked electrical activity embedded in a patient's brain waves may be more accurately detected and analyzed by improving th.e ratio of signal to noise.

It is a further objective of the present invention to provide such a system in which noise which is synchronous with the patient's evoked potentials and within the general range of frequencies of interest may be reduced.

It is a further objective of the present invention to provide such a system in which, automatically and without operator intervention, the "teeth", i.e., the band pass sub-frequencies, are selected to construct a self-optimizing digital comb filter in which some of the sub-frequencies within the range of the filter are band-stopped.

It is a feature of the present invention to provide an electroencephalograph (EEG) system for the detection of a patient's brain waves. The system includes a series of electrodes, for example, the 19 electrodes of the International 10/20 System, adapted to be connected to different sectors of the patient's head. Analog signals representing the patient's brain waves are detected by the electrodes and amplified by amplifier means connected to the electrodes. The amplifier means includes low-noise high-gain amplifiers. The system also includes means for generating visual, auditory or somatosensory electrical stimuli and analog/digital conversion means connected to the amplifiers which produce synchronous sets of digital data corresponding to the patient's brain waves, time-locked to the stimuli (evoked potentials).

A digital comb filter means is connected to the aanlog/digital conversion means to improve the signal-to-noise ratio of the digital data. Digital data analysis means is connected to the comb filter to analyze the data and produce statistically analyzed data showing abnormalities and normalities in the brain waves relative to population norms or reference data obtained from the patient at some earlier time, preferably under anesthesia but prior to the surgical intervention. That analyzed data is shown in display means, such as a CRT monitor or a printer.

The digital comb filter has self-optimizing means to automatically select the band-pass frequencies constituting the teeth of the optimal comb filter. That selection is based on a comparison, at each tooth, of the digital data in the presence and absence of a synchronized stimulus producing an evoked potential brain wave.

BRIEF DESCRIPTION OF THE DRAWINGS

Other objectives and features of the present invention will be apparent from the following detailed description taken in conjunction with the accompanying drawings.

In the drawings:

In FIG. 4, all power in the frequency of any tooth in the comb is passed if the F-ratio exceeds the threshold. In FIG. 5, the amount of power passed is modulated, proportional to the F-ratio for S/N at each frequency within the tooth.

DETAILED DESCRIPTION OF THE INVENTION

Figure 1:
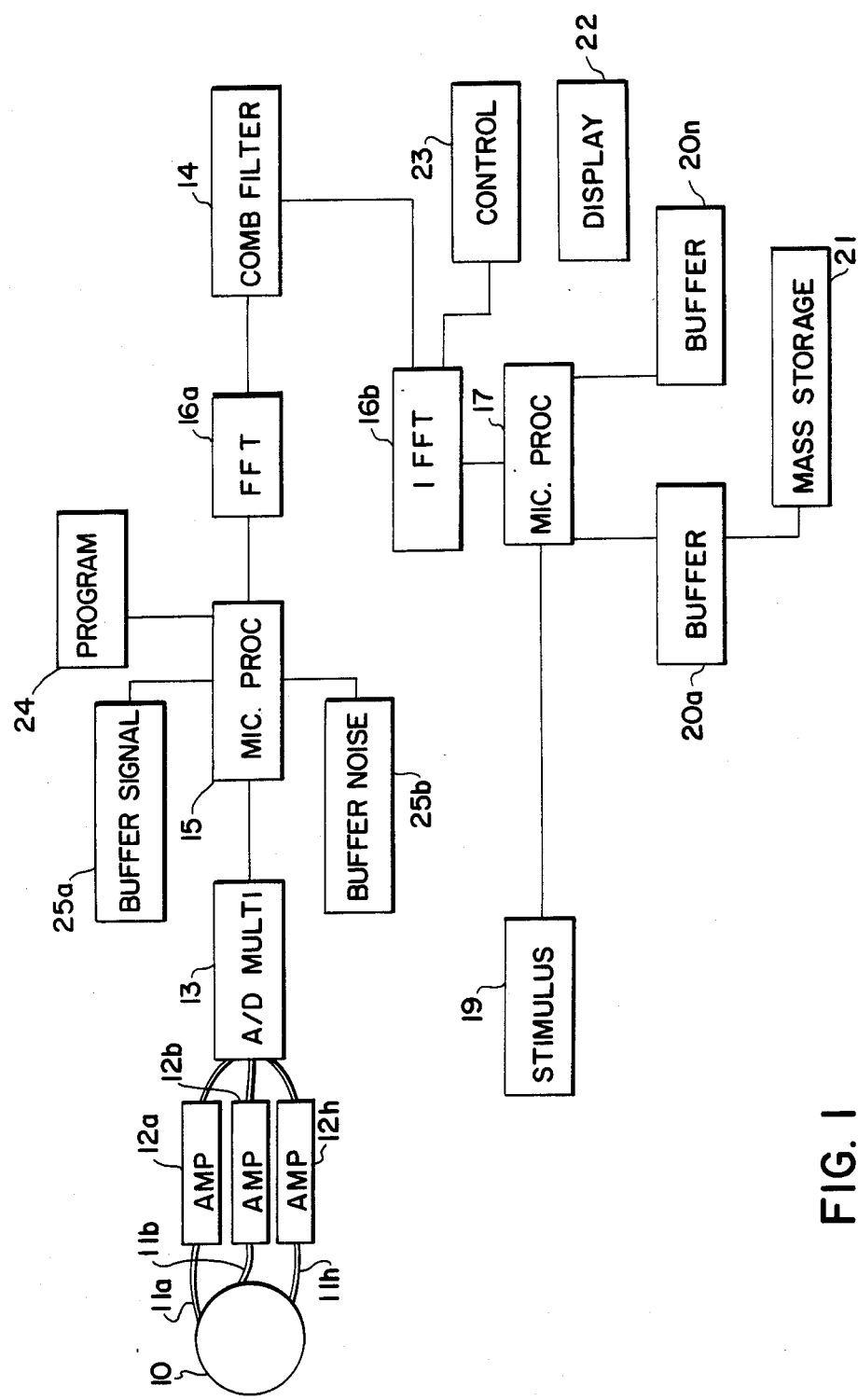
FIGS. 1 and 6 are block diagrams of the system of the present invention.

As shown in FIG. 1, the patient (subject) is positioned so that his head 10 is connected with the desired number of electrodes 11a-11h. The drawing, for simplicity, shows only three pairs of electrodes 11a, 11b and 11h. Alternatively, and not shown, 19 electrodes may be arranged so that the conventional EEG International 10/20 electrode system and nomenclature may be employed. Alternatively, when surgical conditions restrict access to some regions of the head, one active electrode may be located at the vertex or on the forehead and reference electrodes on one or both mastoid processes, behind the ears.

The electrode pairs 11a-11h are connected to respective differential amplifiers 12a-12h, each pair of electrode leads being connected to its own amplifier. Each amplifier 12a-12h has an input isolation switch, such as a photo-diode and LED coupler, to prevent current leakage to the patient. The amplifiers 12a-12h are high-gain low-noise amplifiers, for example, having a frequency range of 0.5 to 5000 Hz, gain of 100,000 common mode rejection of 100 dB and noise of less than 2 microvolts peak-to-peak.

Figure 6:
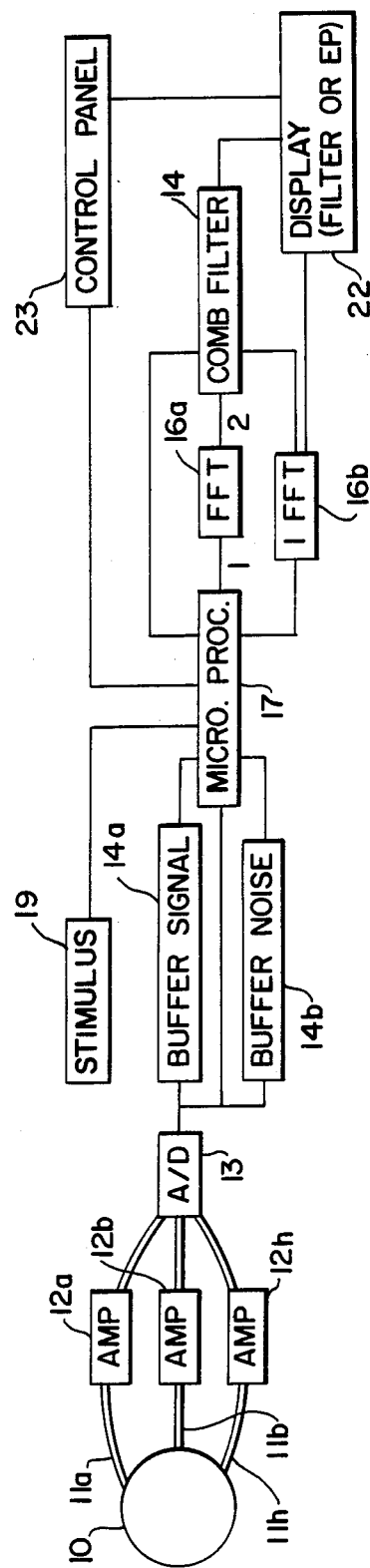

The amplifiers 12a-12h are connected to analog-to-digital multiplexer 13 (A/D multiplexer). The multiplexer 13 samples the amplified analog brain waves at a rate compatible with the bandwidth of the amplifiers, for example, at 100,000 per second with 12-bit resolution. The multiplexer 13 provides, at its output, sets of digital data, representing the EEG analog signal. The multiplexer 13 is connected to "buffer signal" 25a, which stores the signal and "buffer noise" 25b, which stores the noise. The buffers 25a, 25b are connected, and A/D multiplexer is directly connected, to the dedicated microprocessor 15. The dedicated microprocessor 15 is connected through its dedicated 512-point FFT 16a (Fast Fourier Transform) to digital comb filter 14, which is described in detail below. Alternatively, as shown in FIG. 6, the system microprocessor 17 may be used to control the comb filter 14.

The comb filter is connected to, and controls, the IFFT 16b (Inverse Fast Fourier Transform). The output of IFFT 16b is connected to the system microprocessor 17 which is connected to the stimulus devices 19 (lights, loudspeaker, shock device, etc.), to the system digital storage buffers 20a-20n (only two being shown), to the mass storage 21, such as a laser device storage or hard disk, to the display 22, such as a CRT and a matrix print-out recorder and to the control panel 23. Details of these devices will be found in the above-referenced patents and articles.

Figure 2:
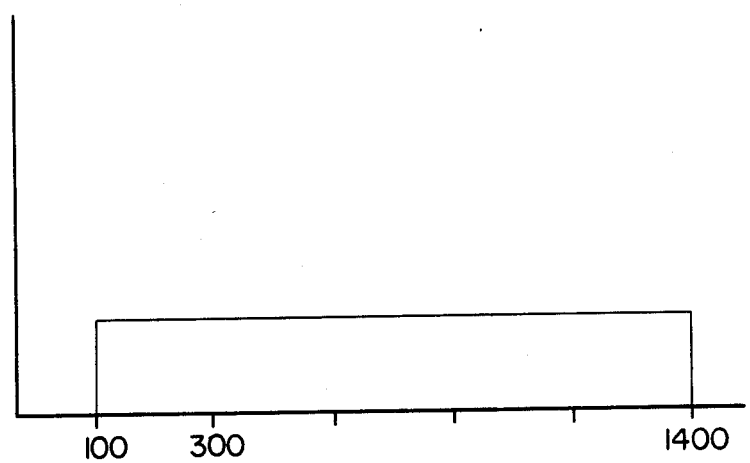
FIG. 2 is a graph showing a prior art band pass

The conventional type of digital filter provides a broad band response, as shown in FIG. 2, in which the frequency response varies successively from zero to a uniform maximum to zero, see Bogner, *Introduction to Digital Filtering*, pages 143–144 (Wiley, 1975).

Figure 3A:
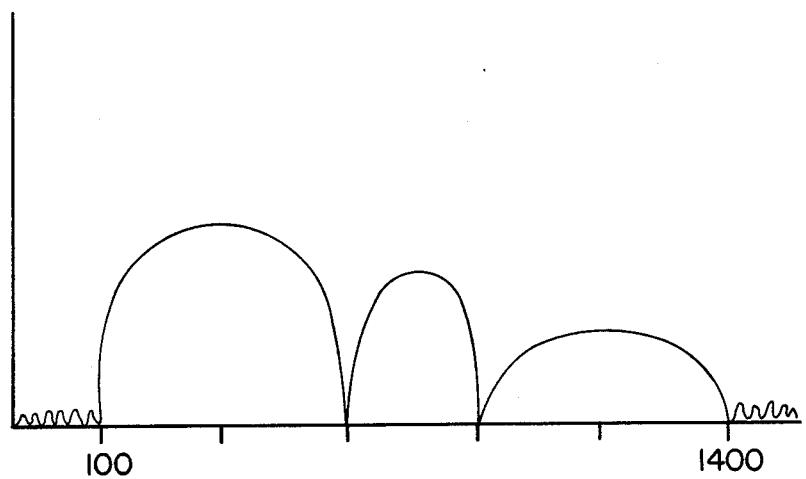
FIG. 3a is a graph showing phase synchrony of a typical signal average.
Figure 3B:
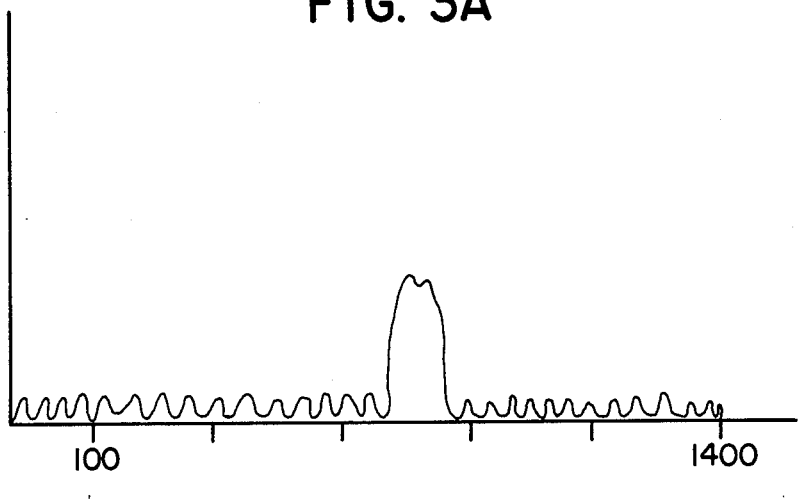
FIG. 3b is a graph showing phase synchrony of a typical noise sample.

FIG. 3a shows the phase synchrony of a typical signal sample having peaks 1, 2 and 3; and FIG. 3b shows the phase synchrony of a typical sample of noise. The "optimum" band filter of the prior art would be as shown in FIG. 2.

Figure 5:
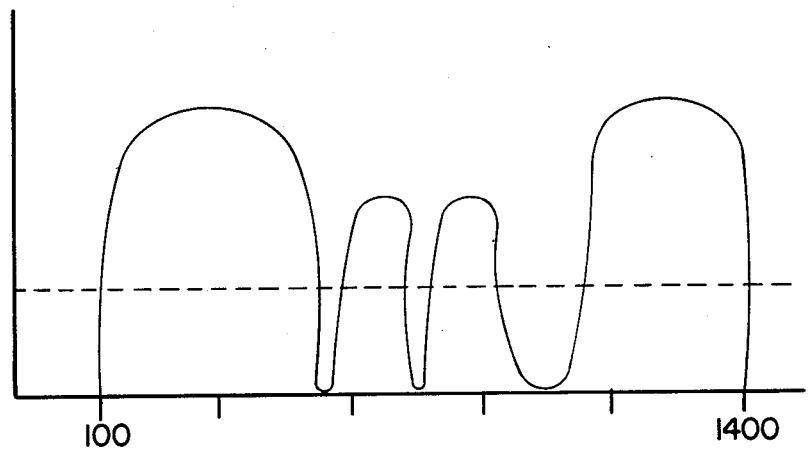
FIGS. 4 and 5 are graphs in which band pass is graphed against frequency, showing alternative comb filters used in the present invention.
Figure 4:
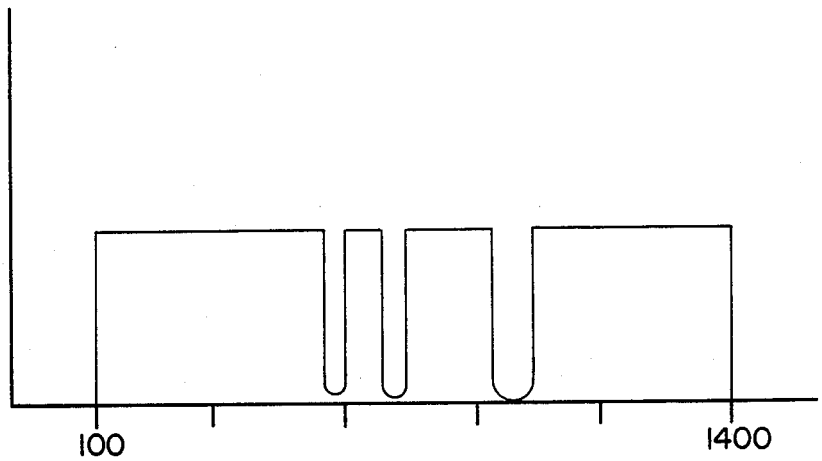

The comb filter of the present invention, shown in FIGS. 4 and 5, may be considered a series of band pass and band stop filters arranged to be responsive over a selected range. As shown in FIG. 4, the selected range is 0–1400 Hz and there are band pass filters at 100–580 Hz, 600–640 Hz and 720–800 Hz and 900–1400 Hz and band-stop filters at 0–100 Hz, 580–600 Hz, 640–720 Hz, 800–900 Hz and above 1400 Hz. The bandpass filters are the "teeth" of the comb and they are selected so as to accord with the frequencies in which the signal/noise ratio is acceptable. The band-stop filters are selected to be at frequencies in which the noise is excessive. The multiplexer is programmed by programmer 24, which may be obtained from a floppy disk, to obtain samples of the signal and of the noise. The noise is preferably obtained when there is an absence of evoked potential stimuli and the signal is obtained during epochs up to 500 milliseconds long, beginning with presentation of the stimuli or after a pre-selected delay.

The noise and signal samples are transformed to their Fourier equivalents (from time domain to phase domain) by Fast Fourier Transform FFT 16a to produce: $a_i + \text{SIN}_{(frequency_i)} + \text{COS (phase}_i)$.

The "phase variance parameter" is computed separately for the signal samples and for the noise samples The "F ratio" is then computed by microprocessor 15 for each narrow frequency band ("subfrequency band") obtained in the FFT. The 'phase variance parameter is defined as follows:

Phase variance parameter (VAR) ($\psi$ i) is calculated from the following formula (the formula gives the phase variance parameter for the ith component of the spectrum).

$$\text{VAR } (\psi i) = \frac{1}{10} \sum_{j=1}^{10} |h_{ij} - \bar{h}_i|^2$$

where $$h_{ij} = \frac{H_{ij}}{|H_{ij}|} \quad \bar{h}_i = \frac{1}{10} \sum_{j=1}^{10} h_{ij}$$

$H_{ih}$ = spectral component of the $j^{th}$ trial (complex value)

The "F" ratio is defined as the ratio of "phase-variance with stimulus: phase-variance without stimulus" and corresponds to the F-ratio used in the analysis of variance (ANOVA).

The formula is as follows:

F = VAR ($\psi$ i): VAR ($\psi$ i')

where the I frequency component is with stimuli and the i' frequency component is without stimuli.

If the F ratio is high, there is a high synchronization of the spectral component with the beginning of the sample in the presence but not in the absence of stimulation, and the signal-to-noise ratio is high. Conversely, if the F ratio is low, there is no significant difference in phase variance whether signal is present or absent; the signal-to-noise ratio is poor. For example, in the case of an EEG instrument the "with stimulus" may be the brain wave signal evoked response (ER) obtained with the presence of a stimulus and "without stimulus" is the brain wave signal without such stimulus. The F ratio is evaluated by microprocessor 15 under control of program 14 at each narrow frequency band (subfrequency band). A threshold is set by the program 14, which has been selected so as to be completely automatic in operation. Alternatively, the threshold may be set by the operator by means of the control panel 23.

If the F ratio is below the threshold at a given narrow frequency band, that narrow frequency band is excluded, by microprocessor 15, from the inverse transform. If the threshold is exceeded, that frequency is included in the inverse transform, as shown in FIG. 4.

As an alternative, as shown in FIG. 5, it may be advantageous to weight the contribution of each accepted "tooth" (narrow band pass) proportional to the value of the F ratio when the inverse transform is performed. The total used signal is a combination of the weighted frequency components represented by all of the accepted teeth of the comb filter, as shown in FIG. 6.

It may, or may not, be advantageous to disqualify from acceptance as a tooth any frequency component for which the signal contains less than a predetermined percentage of the total signal energy or for which the noise contains more than a predetermined percentage of the total noise energy. Such advantage might be present in various applications of this system to the processing of other types of information, such as sonar, radar, radio or video signals.

In practice, a period of filter optimization would usually precede the beginning of the surgical procedure, but after anesthesia. The following "self-norm" is envisaged:

(1) Multiple small baseline samples of brain activity would be collected, consisting of brief segments beginning at the time of stimulus onset or after a preselected delay. The elements in each such sample might be combined into a "light average" of size N (SIGNAL SAMPLES).

(2) An equal number of baseline "light averages" of size N would be collected in the absence of stimulation (NOISE SAMPLES).

(3) FFT would be performed separately on each signal sample, and the phase synchrony (1-phase variance) computed as a function of frequency (SIGNAL PHASE SYNCHRONY).

(4) FFT would be performed separately on each noise sample, the phase synchrony computed as a function of frequency (NOISE PHASE SYNCHRONY).

(5) The SIGNAL PHASE SYNCHRONY AND NOISE PHASE SYNCHRONY would be displayed one above the other on the CRT display 22.

(6) The "optimum F-ratio comb filter" (Version 1 see FIG. 4) or "modulated F-ratio comb filter (Version 2 see FIG. 5) would be displayed on display 22 below these, together with the selected threshold.

(7) The unfiltered averaged signal, the signal filtered by operator-selected band, optimal F-ratio comb and/or modulated F-ratio comb are displayed on display 22, aligned vertically one above the other for final approval, if a qualified operator is present. If not, the automatically selected filter would be used.

(8) Once the filter is selected, whether by operator choice or automatically, all baseline SIGNAL samples and NOISE samples would be separately passed through the filter, i.e., the appropriate IFFT would be performed.

(9) Using an automatic peak detector, all maxima (positive peaks) and minima (negative peaks) exceeding the rms mean amplitude of the filtered noise by some threshold, preferably two standard deviations of the rms noise, would be located.

(10) The mean and standard deviation of amplitude and latency would be computed to derive the confidence interval signifying the limits of peak variability expected in subsequent SIGNAL samples. If reliable confidence intervals cannot be found with single "light averages" (each of size N), multiples of 2, 4, 8, etc. light averages should be averaged together and the confidence interval assessed at each successively larger sample size. A "reliable confidence interval" for a sample of n light averages is defined as one for which a peak within some permitted latency range is detected in each of the initial set of SIGNAL samples. This can be done automatically or with operator supervision if available.

(11) Once the optimal filter has been defined and the sample size ascertained for which a reliable confidence interval can be defined for the peak or peaks critical for the purposes of a particular operation, routine monitoring of the EP can begin. Each sample is subjected to FFT, followed by the IFFT defined by the optimum filter, and then subjected to peak detection. Deviation of peak amplitude (AMP) and latency (LAT) are expressed in microvolts and microseconds from the self-norm, or are Z-transformed relative to baseline statistics to permit objective evaluation. Multivariate Z values $(\sqrt{Z^2_{AMP}+Z^2_{LAT}})^{\frac{1}{2}}$ can also be computed. These values are presented in appropriate high-lighted form on the CRT 22 or used for an automatic reporting means to inform the operating room personnel by appropriate visual or auditory signals. Differences between peak latencies or amplitudes may also be used for reporting.

(12) As surgical maneuvers or anesthesia changes cause improvement or deterioration in neural condition, the strength and latency of EP components and their variance may alter Similarly, as operating room apparatus is switched on and off or moved about, environmental noise may change. Ideally, the monitoring apparatus should be coupled to blood pressure, heart rate, and anesthetic level sensing apparatus and should report correlated sources of EP variations. Thus, the true optimum filter may vary repeatedly during the course of an operation, no matter how it is defined.

For this reason, it may be desirable to continuously redefine the optimum filter. An adaptive optimum filter, automatically redefining itself, can be achieved within the present framework by:

(a) Updating the set of SIGNAL samples used to compute SIGNAL PHASE SYNCHRONY (SPS) by dropping out the oldest sample, adding the newest sample and recomputing SPS.

(b) Similarly, at regular intervals (perhaps but not necessarily in alternate time periods), the set of NOISE samples can similarly be updated and NOISE PHASE SYNCHRONY (NPS) recomputed.

(c) Using these sliding window estimates of SPS and NPS, the F-ratio as a function of frequency can be continuously computed and an adaptive optimum comb or F-ratio modulated filter continuously redefined and applied to compute new confidence intervals and to evaluate the next SIGNAL sample.

(d) Means must be provided, should such adaptive filtering be adopted, to protect against gradual steady deterioration by periodic checks against the initial baseline and notification by appropriate means, when such gradual changes have caused significant deviations from the initial baseline. Such a check might be provided by t-tests for the difference between the baseline statistics and the current values for the means and standard deviations of peak latencies and amplitudes.

The above description has been in connection with an electroencephalograph system and method for the detection of a patient's brain waves. However, a system and method utilizing the digital comb filter may be applicable to a radar (radio detection and ranging) system in which the comb filter may be applied in connection with the local oscillator signal.

What is claimed is:

1. An electroencephalograph (EEG) system for the detection of a patient's brain waves, including:

a series of electrodes adapted to be connected to a plurality of sectors of the patient's head to produce analog signals representing the patient's brain waves; amplifier means connected to the electrodes, including low-noise high-gain amplifiers to amplify the analog signals; analog/digital conversion means connected to the amplifiers to produce sets of digital data corresponding to the patient's brain waves;

a digital filter means connected to said analog/digital conversion means to improve the signal-to-noise ratio of the digital data;

digital data analysis means connected to the filter means to analyze the data on a statistical basis to produce analyzed data showing abnormalities and normalities in the brain waves; and display means to display the analyzed data;

wherein said digital filter means is a digital comb filter which has self-optimizing means to automatically select the band pass frequencies constituting the teeth of the comb filter based on a comparison, at each tooth, of the phase variance parameter of digital data in the brain state of the presence and the brain state of the absence of a synchronized stimulus producing an evoked potential brain wave.

2. An electroencephalograph system as in claim 1 and further including proportional teeth selection means which select and adjust the proportion of signals accepted from each tooth of the comb filter based upon the signal noise ratio in each tooth.

3. An electroencephalograph system as in claim 1 and further including FFT (Fast Fourier Transform) means to control the selection of said teeth, wherein said digital data is subjected to FFT for comparison of the different states.

4. An electroencephalograph (EEG) system for the detection of a patient's brain waves, including:

a series of electrodes adapted to be connected to a plurality of sectors of the patient's head to produce analog signals representing the patient's brain waves; amplifier means connected to the electrodes, including low-noise high-gain amplifiers to amplify the analog signals; analog/digital conversion means connected to the amplifiers to produce sets of digital data corresponding to the patient's brain waves; Fast Fourier Transform means connected to said analog/digital conversion means;

a digital filter means connected to said Fast Fourier Transform means to improve the signal-to-noise ratio of the digital data; Inverse Fast Fourier Transform means connected to and controlled by the digital filter means;

digital data analysis means connected to the Inverse Fast Fourier Transform means to analyze the data on a statistical basis to produce analyzed data showing abnormalities and normalities in the brain waves; and display means to display the analyzed data;

wherein the digital filter means is a digital comb filter having self-optimizing means to automatically select the band pass frequencies constituting the teeth of the comb filter based on a comparison, at each tooth, of the phase variance parameter of digital data in the brain state of the presence and the brain state of the absence of a synchronized stimulus producing an evoked potential brain wave.

5. An electroencephalograph system as in claim 4 and further including proportional teeth selection means which select and adjust the proportion of signals accepted from each tooth of the comb filter based upon the signal noise ratio in each tooth.

6. The method of improving the signal/noise ratio in an electroencephalograph (EEG) system for the detection of a patient's brain waves, including:

connecting a series of electrodes to a plurality of sectors of the patient's head to receive analog signals representing the patient's brain waves; amplifying the brain wave signals using low-noise high-gain amplifiers; producing sets of digital data corresponding to the patient's brain waves by analog/digital conversion means connected to the amplifiers;

improving the signal-to-noise ratio of the digital data by a digital comb filter connected to said analog/digital conversion means;

analyzing the data on a statistical, basis to produce analyzed data showing abnormalities and normalities in the brain waves by digital data analysis means connected to the digital comb filter; displaying the analyzed data on display means;

automatically, and using self-optimizing means, selecting the band pass frequencies constituting the teeth of the comb filter based on a comparison, at each tooth, of the phase variance parameter of digital data in the brain state of the presence and the brain state of the absence of a synchronized stimulus producing an evoked potential brain wave.

7. The method of claim 6 and including the steps of:

defining the optimum comb filter by obtaining samples of signal during stimulation and samples of noise in the absence of stimulation;

obtaining the phase synchrony on said signal and noise samples using Fast Fourier Transform; and in the course of the procedure, updating the obtaining of samples and phase synchrony to re-define the comb filter.

* * * * *